United States Patent

Cox et al.

Patent Number: 6,025,522
Date of Patent: Feb. 15, 2000

[54] PROCESS FOR MAKING SECONDARY AMPHOACETATES AND DIACETATES

[75] Inventors: Graham Cox, Huddersfield, United Kingdom; Torsten Henning, Kelkheim, Germany

[73] Assignee: Clariant Finance (BVI) Ltd., Tortola, Virgin Islands (Br.)

[21] Appl. No.: 09/302,606

[22] Filed: Apr. 30, 1999

[51] Int. Cl.[7] .......................... C07C 51/16; C07C 229/22; C07C 229/30

[52] U.S. Cl. ............................... 562/526; 562/564

[58] Field of Search ...................... 562/529, 564

[56] References Cited

PUBLICATIONS

Database CAPLUS on STN, Acc. No. 1992:407492, Sotodani et al., 'Preparation fo amindoamine compounds with low discoloration.' JP 04026663 A2 (abstract), 1992.

*Primary Examiner*—Gary Geist
*Assistant Examiner*—Brian J. Davis
*Attorney, Agent, or Firm*—Miles B. Dearth

[57] ABSTRACT

Process for making secondary amphoacetate and amphodiacetate of the formula

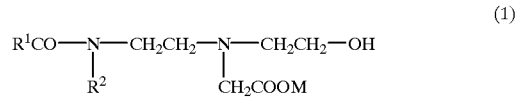

(1)

wherein $R^1$ is $C_8$–$C_{18}$-alkyl or $C_8$–$C_{18}$-alkenyl, $R^2$ is hydrogen or a group of the formula —$CH_2COOM$ and M is alkaline or alkaline earth metal, which comprises heating a compound of the formula 2

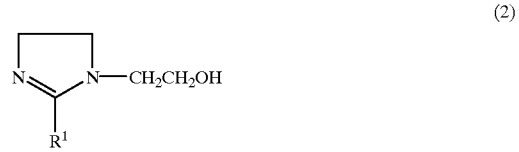

(2)

at pH between 7–14, at a temperature of 80 to 90 deg C. and for at least 24 hours and subsequent reaction with an aqueous solution of chloroacetic acid or is alkali salt at a pH from 7 fo 14 and a temperature of 80 to 90° C. Due to the long period for the ring opening in the first step predominantly secondary products are obtained which are advantageous in that they show a low viscosity of their aqueous solution.

1 Claim, No Drawings

PROCESS FOR MAKING SECONDARY AMPHOACETATES AND DIACETATES

BACKGROUND OF THE INVENTION

Amphoacetates are a well known group of surfactants (see U.S. Pat. No. 5,744,063, DE 36 39 752, DE 196 36 205, DE 43 07 709 and DE 42 40 154). These amphoacetates are made by reacting 1-hydroxyethyl-2-alkyl-2-imidazoline with chloroacetic acid or the alkali salt thereof. This reaction, however, does not yield a single product but a ring-opening of the imidazoline yields a mixture of the secondary monoamide and the tertiary monoamide of the formulae

and

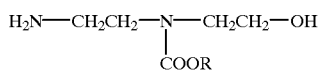

Subsequent reaction with chloroacetic acid or chloroacetate yields the corresponding mixture of secondary and tertiary amphoacetates. These mixtures of amphoacetates, however, have a decisive drawback in that the viscosity of aqueous solutions of such mixtures of amphoacetates increases upon storage.

Thus the problem was to make amphoacetates which avoid such increase in viscosity. Based on kinetic investigations into the hydrolysis of the imidazoline starting product by means of NMR spectroscopy it has been found that under the conditions as stated below predominantly secondary amphoacetates can be produced, the aqueous solutions thereof retain their low viscosity even upon prolonged storage.

SUMMARY OF THE INVENTION

Subject matter of this invention is a process for making secondary amphoacetate and amphodiacetate of the formula 1

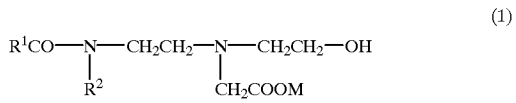

wherein $R^1$ is $C_8$–$C_{18}$-alkyl or $C_8$–$C_{18}$-alkenyl, $R^2$ is hydrogen or a group of the formula —$CH_2COOM$ and M is alkaline or alkaline earth metal. The process comprises the controlled alkaline hydrolysis of a compound of the formula 2.

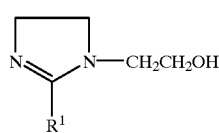

The hydrolysis occurs at a pH between 7–14, at a temperature of 80 to 90 deg C. and a reaction time of at least 24 hours. The resultant secondary amide of formula 3

can be cleanly converted "in situ" to the corresponding secondary amphoacetate or diacetate by reaction with an aqueous solution of chloroacetic acid or its alkali salt at a pH from 7 fo 14 and a temperature of 80 to 90° C.

The imidazoline compounds of formula 2 are made by reacting aminoethyl-ethanolamine with a fatty acid or mixtures thereof having the carbon atom range indicated above. Examples of single fatty acids and fatty acid mixtures that can be used to prepare the imidazolines can include coconut oil fatty acid, palm kernel oil fatty acid, capric caproic, caprylic, hexadecadienoic, lauric, linoleic, linolenic, margaric, myristic, myristoleic, oleic, palmitic, palmitoleic, stearic and the like.

The formation of the imidazoline compound of formula 2 is made by heating the fatty acid(s) with the aminoethyl-ethanolamine according to processes known per se, for example by heating a mixture of one mole fatty acid(s) with 1 to 2.5 mole of aminoethyl ethanolamine first at a temperature of 150 to 1 80° C., and subsequently to 180 to 230° C. under reduced pressure to remove the water formed in the reaction (DE 43 07 709).

This imidazoline compound is ring opened under controlled conditions to yield predominantly (>95%) the secondary amide ( pH 7 to 14, preferably pH 8 to 9, and at 80 to 90 deg C. for at least 24 hours ). When this 24 hour minimum hydrolysis time is completed, the addition of the monochloroacetate takes place. This is conducted at pH 8–12 and at 85 deg C. Processing for this stage will take up to 24 hours, but more typically 8–12 hours. Stage 1 (above) allows control of the product to only one pure (>95%) species (secondary amide amine, formula 3 ) thus enabling step 2 of the process to be conducted with a smaller optimum excess of monochloroacetate yielding high (80–90%, typically 85%) levels of mono acetate product in the final product. This is confirmed by quantitative high resolution NMR experiments.

DESCRIPTION OF THE PREFERRED EMBODIMENTS

Generally the ratio of monochloroacetate to compound of formula (1) is 1.15 to 1.0 for the mono-acetate and 2.1 to 2.0 for the di-acetate.

The resulting aqueous solution of the secondary amphoacetate or di-acetate can be used as such or they can be further diluted with water or suitable organic solvents such as glycerol, ethylene glycol, propyleneglycol, diethyleneglycol or their mono- or diether derivatives. Due to the fact that these solutions essentially contain only the secondary amphoacetates the viscosity of these solutions does not rise upon storage.

The pure amphoacetate surfactants of the present invention are extremely mild and non-irritating to both eyes and skin. They also exhibit enhanced wetting speed, greater surface tension reduction, high foaming and foam stabilization properties, low toxicity, and excellent compatibility with other anionic, ionic and nonionic surfactants. These products are stable over a wide pH range and are biodegradable. These properties make these surfactants adaptable for use in products ranging from cosmetics to industrial applications and are usable wherever amphoacetate surfactants of this type have found use. These products are particularly useful for non-irritating shampoos, including baby shampoos, body shampoos including bubble baths, bar soaps, bath gels, hair conditioning gels, lotions, skincreams and lotions, make up removal creams and lotions, liquid detergents, dish detergents and other washing and cosmetic products that contact the skin.

The influence of temperature and reaction time on the ring opening of the imidazoline were investigated by H- and C-NMR spectroscopy. This revealed the following amounts of secondary and tertiary monoamide from which the final products are derived by reaction with chloroacetic acid or its alkali salt:

|  | 60° C./pH 7–8 | | 85° C./pH 7–8 | |
| --- | --- | --- | --- | --- |
| Reaction Time | Mol-% sec. Monoamid | Mol-% tert. Monoamid | Mol-% sec. Monoamid | Mol-% tert. Monoamid |
| 3 h | 69 | 31 | 74 | 26 |
| 7 h | 71 | 29 | 86 | 14 |
| 24 h | 81 | 19 | 97 | 3 |

This analysis shows that almost pure secondary product can only be obtained under the conditions as specified above that means at a temperature of at least 80° C. and a reaction time of a least 24 hours.

EXAMPLE 1

602 g (mol wt 268, 2.246 mols) $C_{12}$ (lauryl) Hydroxy Ethyl Imidazoline was melted at 40–50 deg C. and charged to a 5 liter round bottom flask equipped with stirrer, temperature indication and nitrogen feed. To this stirred melt was added 1400 g fully de-ionised water. The resultant milky emulsion had approximate pH of 11. This then was slowly warmed under a nitrogen blanket with moderate agitation to 80–85 deg C. When this temperature range was achieved the flask was maintained for a further 20–24 hours.

Analysis of the product achieved showed pH 9.7, water content 67.4% and viscosity 10 cps (@ 40 deg C.). The 400 MHz NMR shows secondary amide amine >95%.

There was 645 g ( mol wt 286, 32% solution equivalent to 0.7217 mols ) of this resultant solution transferred to a 2 liter flask and maintained under nitrogen at 50–55 deg C. and the pH trimmed to 8.5–9.0 with a little (0.25 g) citric acid. There was added 60 g water for additional dilution. When the temperature and pH were stable the charge of sodium monochloroacetate was begun. In total there was charged 96.3 g (mol wt 116.5, 0.8266 mol, 1.15 equivalents) of sodium monochloroacetate powder (SMCA) over a period of 2 hours. The pH was controlled manually during charging of SMCA every 15 minutes with addition of 32% caustic soda to maintain the pH within the range 8.5–9.0. The temperature required control during SMCA addition with cooling to maintain the temperature within the range 50–60 deg C. Following 30 minutes of the last charge of SMCA the flask was gently heated to raise the temperature to 80–85 deg C. The control of pH was maintained at 8.5–9.0 throughout this stage of the process. After 6 hours the measurement of residual SMCA indicated a level of approximately 1000 ppm. The pH at this stage was raised to a level of 11.5–12.0. The process was maintained at this level for a further 3 hours until the SMCA level was measured at <20 ppm. The total 32% caustic soda usage during the pH control was 103 g (0.824 mols). The product was cooled and the pH trimmed with citric acid (approximately 2 g ) to the range 9.5–10.5.

Final analysis showed a product that was a clear pale yellow liquid with the following characteristics:

appearance clear pale yellow liquid colour approximately iodine 4

Viscosity 1220 cps at 20 deg C.

SMCA <20 ppm

Sodium Dhloride 5.58% pH (5%) 10.23

Specific gravity 20° C. 1.1139 g/cc

NMR 400 MHz 85% Mono acetate, <=5% non-alkylated, 10% diacetate

We claim:

1. Process for making secondary amphoacetate and amphodiacetate of the formula

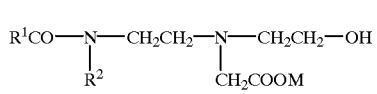

(1)

wherein $R^1$ is $C_8$–$C_{18}$-alkyl or $C_8$–$C_{18}$-alkenyl, $R^2$ is hydrogen or a group of the formula —$CH_2COOM$ and M is alkaline or alkaline earth metal, which comprises heating a compound of the formula 2

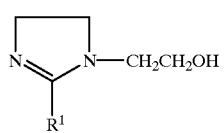

(2)

at pH between 7–14, at a temperature of 80 to 90 deg C. and for at least 24 hours and subsequent reaction with an aqueous solution of chloroacetic acid or its alkali salt at a pH from 7 to 14 and a temperature of 80 to 90° C.

\* \* \* \* \*